(12) United States Patent
Kayani

(10) Patent No.: US 8,987,676 B2
(45) Date of Patent: Mar. 24, 2015

(54) SYSTEM AND METHOD FOR THE DETECTION OF SOILING IN BANK NOTES

(75) Inventor: Sohail Kayani, Irving, TX (US)

(73) Assignee: Toshiba International Corporation, Houston, TX (US)

( * ) Notice: Subject to any disclaimer, the term of this patent is extended or adjusted under 35 U.S.C. 154(b) by 349 days.

(21) Appl. No.: 13/559,989

(22) Filed: Jul. 27, 2012

(65) Prior Publication Data

US 2014/0027649 A1    Jan. 30, 2014

(51) Int. Cl.
G01J 1/42 (2006.01)
G01N 21/33 (2006.01)
G07D 7/12 (2006.01)
G07D 7/18 (2006.01)

(52) U.S. Cl.
CPC ............. *G01J 1/429* (2013.01); *G01N 21/33* (2013.01); *G07D 7/12* (2013.01); *G07D 7/187* (2013.01)
USPC ...................................................... 250/372

(58) Field of Classification Search
USPC ...................................................... 250/372
See application file for complete search history.

(56) References Cited

U.S. PATENT DOCUMENTS

| 5,915,518 | A * | 6/1999 | Hopwood et al. ............. 194/207 |
| 5,960,103 | A | 9/1999 | Graves et al. |
| 6,351,552 | B1 | 2/2002 | Weaver et al. |
| 7,378,665 | B2 * | 5/2008 | Schuett et al. .................. 250/372 |
| 7,938,274 | B2 | 5/2011 | Yui |
| 2003/0042438 | A1 | 3/2003 | Lawandy et al. |
| 2005/0173221 | A1 | 8/2005 | Maier et al. |
| 2006/0115139 | A1 | 6/2006 | Joshi et al. |
| 2007/0071302 | A1 | 3/2007 | Jones et al. |
| 2008/0006505 | A1 | 1/2008 | Renz et al. |
| 2010/0032351 | A1 | 2/2010 | Schmidt |
| 2010/0128964 | A1 | 5/2010 | Blair |
| 2010/0206779 | A1 * | 8/2010 | Blair et al. .................... 209/534 |
| 2012/0176605 | A1 | 7/2012 | Stoeckli et al. |

FOREIGN PATENT DOCUMENTS

EP      1785951 A1    5/2007
WO      94/16412 A1   7/1994

OTHER PUBLICATIONS

International Search Report and Written Opinion issued in related International Application No. PCT/US2013/051962, mailed Feb. 21, 2014, 10 pages.

* cited by examiner

*Primary Examiner* — David Porta
*Assistant Examiner* — Mindy Vu
(74) *Attorney, Agent, or Firm* — Baker Botts L.L.P.

(57) ABSTRACT

A method for handling soiled bank notes is disclosed. The method includes directing a bank note to an ultraviolet detector; transmitting an ultraviolet signal from the ultraviolet detector to the bank note; receiving a reflected ultraviolet signal from the bank note at the ultraviolet detector; analyzing the reflected ultraviolet signal; identifying a soiling level for the bank note based on analysis of the reflected ultraviolet signal; and handling the bank note based on the identified soiling level. Analyzing the reflected ultraviolet signal can include comparing a characteristic of the reflected ultraviolet signal with calibration data. The calibration data can be stored in a computer-readable medium. The bank note is identified as a soiled bank note if the identified soiling level exceeds a threshold soiling level.

15 Claims, 3 Drawing Sheets

SYSTEM AND METHOD FOR THE DETECTION OF SOILING IN BANK NOTES

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE DISCLOSURE

1. Field of the Disclosure

The present disclosure relates to automated currency processing and, more specifically, to the automated detection of soiling in bank notes undergoing high-speed processing.

2. Description of Related Art

Once a bank note is issued and circulated it is often transferred amongst a number of individuals and entities. With time, the bank notes are likely to become soiled. Specifically, soiled bank notes are bank notes which have become dirty and/or limp due to excessive use. For instance, the bank notes are often handled by individuals and contact with human fingers is a major source of bank note soiling. As body oils are deposited on the bank notes due to human contact, they facilitate adherence of dust and dirt to the bank notes. Moreover, bank notes are often crumbled or folded during every day use further contributing to the bank note deterioration.

In an effort to maintain a desired standard for the bank notes in circulation, banks often remove bank notes that have been soiled beyond a threshold level and are deemed unusable. These notes are then removed from circulation and replaced with new bank notes. Accordingly, it is desirable to provide an automated mechanism for identifying and/or setting a side bank notes that are soiled and need to be replaced.

These and other improvements will become apparent when the following detailed disclosure is read in light of the supplied drawings. This summary is not intended to limit the scope of the disclosure to any particular described embodiment or feature. It is merely intended to briefly describe some of the key features to allow a reader to quickly ascertain the subject matter of this disclosure. The scope of the disclosure is defined solely by the claims when read in light of the detailed disclosure.

BRIEF DESCRIPTION OF THE SEVERAL VIEWS OF THE DRAWING(S)

The present disclosure will be more fully understood by reference to the following detailed description of the preferred embodiments of the present disclosure when read in conjunction with the accompanying drawings, in which like reference numbers refer to like parts throughout the views, wherein.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description, and all changes which come within the meaning and range of equivalency of the claims are therefore intended to be embraced therein.

DETAILED DESCRIPTION OF THE DISCLOSURE

The present disclosure utilizes a novel method for identifying soiled bank notes by utilizing an ultraviolet detector which is operable to transmit and receive ultraviolet signals and identify soiled bank notes based on the received ultraviolet signals.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires, optical fibers, microwaves, radio waves, and other electromagnetic and/or optical carriers; and/or any combination of the foregoing.

Figure 1:
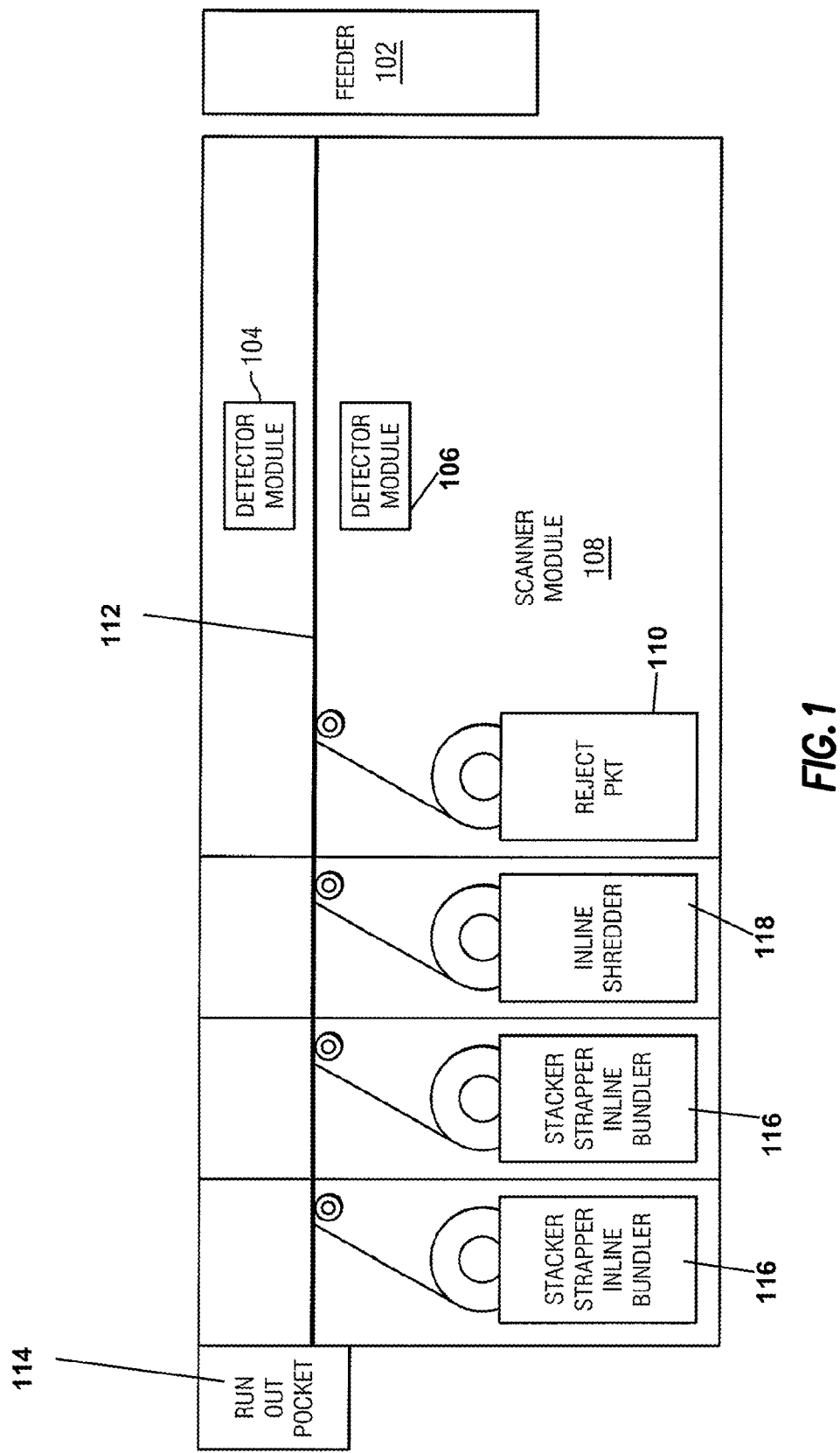
FIG. 1 depicts a block diagram of a basic bank note processing machine, illustrating the location of detectors within the processing stream.

FIG. 1 depicts a block diagram of a bank note processing machine according to one embodiment of the present disclosure, highlighting the location of the detectors with respect to the processing stream. A bank note is first stripped from a stack of notes in the feeder (102) and sent along the transport path to the scanner module (108). Within the scanner module (108) is an area centered on the transport path in which one or more detectors may be located. In accordance with an embodiment of the present disclosure, the detectors (104, 106) may be ultraviolet detectors which may check the note for soiling. As would be appreciated by those of ordinary skill in the art, with the benefit of this disclosure, other detectors such as optical detectors and/or ultrasonic detectors may also be included in the scanner module (108) in order to identify damaged notes or other desirable characteristics. As discussed in more detail below, if it is determined that the note is soiled beyond a preset threshold, it may be marked accordingly and be directed to a special pocket (110) for replacement or otherwise removed from the processing stream and placed into a reject pile.

A transport device or belt (112) is provided along which notes travel past the ultraviolet detectors (104, 106). The notes are then directed to a final disposition component, which typically comprises a pocket (114) for collection of processed notes, one or more strappers (116) for strapping the notes in bundles, and a means for depositing the notes into the pocket by pulling the notes from the note processing path or transport device. The soiled notes identified by the ultraviolet detectors (104, 106) may be directed to a designated pocket (110) where they may be replaced with new notes and then be rejected or they may be directed to an inline shredder (118) where they are shredded.

Processing of the bank notes may be controlled by a central processor (120), which may be an information handling system that controls the timing of the system as well as activation of the detectors and control of the note disposition. However, one of ordinary skill will appreciate that the central processor (120) may be either a single processing unit or it may consist of multiple processors. Computer-readable media may also be present, providing storage capacity for the computer code which controls the processor's actions as well as pre-set values such as the threshold values discussed in further detail below. The central processor (120) is capable of running the stored program steps from the accessible memory. As discussed above, the information handling system acting as the central processor (120) may be a dedicated general purpose computer, an embedded RISC or CISC computer processor, a DSP, or the like.

Figure 2:
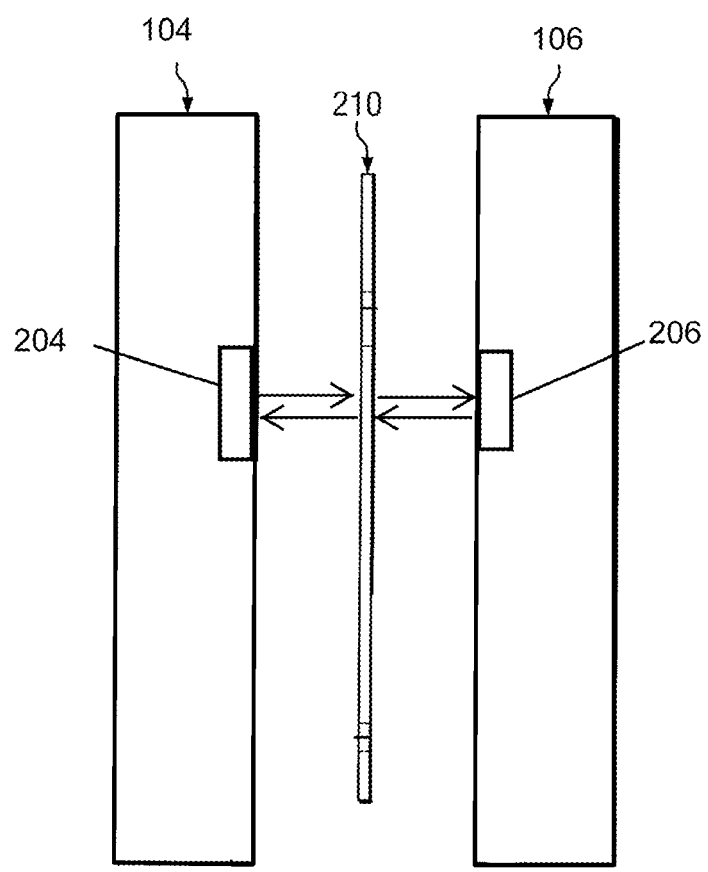
FIG. 2 depicts a close-up view of an ultraviolet detector in additional detail.

FIG. 2 is a close-up view of the ultraviolet detectors (104, 106) in accordance with an embodiment of the present disclosure depicting a bank note (210) passing therebetween. Each ultraviolet detector (104, 106) may include a transceiver (204, 206) coupled thereto. Although one transceiver is depicted on each ultraviolet detector (104, 106), in other embodiments a plurality of transceivers may be used in conjunction with each ultraviolet detector (104, 106) to provide redundancy and improve accuracy. The transceivers (204, 206) may transmit ultraviolet signals and receive a reflected ultraviolet signal as shown by arrows in FIG. 2. As would be appreciated by those of ordinary skill in the art, with the benefit of this disclosure, instead of using a transceiver to both transmit and receive signals, in other embodiments pairs of transmitters and receivers may be used without departing from the scope of the present disclosure. The bank note transport path (112) along which the bank note (210) travels is positioned so that the bank note (210) travels between the two ultraviolet detectors (104, 106) and corresponding transceivers (204, 206).

Often, bank note soiling is result of deposition of biological residue thereon. Such biological residues fluoresces when exposed to UV light. Accordingly, a measurement of reflected fluoresces from the surface of a bank note provides an accurate indication of amount and type of biological residue thereon and thus, the amount of bank note soiling. Accordingly, the ultraviolet detectors (104, 106) may transmit a UV light having a suitable wavelength that is reflected by the biological residue on the bank note. In certain embodiments, a UV light having a wavelength between approximately 280 nm and 380 nm is transmitted by the ultraviolet detectors (104, 106) to capture an image of biological residue. The reflected light from the surface of the bank note may be in a range extending between visible light and near infra red, depending on the nature of materials thereon. The wavelength of the reflected light may provide an indication of the nature of residual contaminants on the bank note surface. For instance, in certain embodiments, a reflected wave having a wavelength of approximately 470 nm may be indicative of human biological contamination.

In certain embodiments, one or more photodetectors may be integrally associated with the ultraviolet detectors (104, 106) or otherwise coupled thereto to receive the reflected light from the surface of the bank notes. The photodetector may detect the intensity of the reflected light emitted by the surface. In one embodiment, an electrical output by the photodetector may be indicative of the intensity of the reflected light. The ultraviolet detectors (104, 106) may be calibrated in advance using bank notes with known soiling. Specifically, different "soiling levels" may be set in advance for different levels of bank note contamination and the soiling levels and the intensity of reflected light corresponding to each soiling level (or other characteristics of the reflected light) may be stored as calibration data in a computer-readable medium accessible to the central processor (120) or another information handling system. The ultraviolet detectors (104, 106) may then be communicatively coupled to the information handling system and use the calibration data to identify a soiling level for each bank note based on a comparison of the characteristics of the reflected light from the bank note with the calibration data.

The identified soiling level may then be utilized by the bank note processing machine to determine how to handle the bank notes. For instance, in certain embodiments, a particular soiling level may be set as the threshold soiling level and all bank notes with a detected soiling level falling below that threshold may be deemed fit for use while bank notes with a soiling level exceeding that threshold may be deemed unfit and be disposed of. The number of soiling levels set and the characteristics of each level may be determined based on the particular application and user preferences. For instance, in certain embodiments, there may be only two soiling levels, the first corresponding to a bank note with an acceptable soiling level and the second corresponding to a bank note with an unacceptable soiling level. In other embodiments a plurality of soiling levels may be designated.

In certain embodiments, calibration data may be obtained by performing a linear regression on multiple points of different bank notes with known soiling levels to determine a relationship between soiling and the reflected light in response to irradiating the bank note with UV light of a given wavelength.

In certain embodiments, the bills may be sorted based on their soiling levels and handled accordingly. Moreover, the ultraviolet detectors (104, 106) may be arranged to irradiate all or a portion of the surface of a bank note without departing from the scope of the present disclosure. In certain embodiments, a more accurate soiling analysis may be performed by irradiating white portions of a bank note which are devoid of ink or other markings. As would be appreciated by those of ordinary skill in the art, the bank note processing machine may be customized based on known printing on the bank notes being analyzed to achieve this arrangement.

Returning now to FIG. 2, as the bank note (210) passes along the path (112) between the first ultraviolet detector (104) and the second ultraviolet detector (106), the first transceiver (204) and the second transceiver (206) monitor the reflection of the ultraviolet signals from the opposing surfaces of the bank note (210). The analysis of the reflected ultraviolet signals may be used to determine whether the bank note (210) is soiled beyond a preset threshold.

The ultraviolet signal (or ultraviolet light) possesses a number of characteristics making it particularly effective for detection of soiled bank notes. First, ultraviolet signals do not penetrate even very thin layers of materials, making surface topology more apparent. Moreover, the ultraviolet signal is highly absorbed by many commonly encountered organic materials but is reflected by inorganic materials such as dust and other surface contamination. Therefore, if organic materials are present on a surface with a relatively high ultraviolet reflectance, the substances will often stand out more strongly than they would if visible light or infrared light was used. Moreover, because of its short wavelength, the ultraviolet light is scattered much more readily by small surface imperfections on a smooth surface as compared to visible light or infrared light. As a result, the ultraviolet signal is particularly effective for detecting scratches or dust on the bank note surfaces.

In certain embodiments, the ultraviolet detectors' (104, 106) source of UV light may remain on while the bank note processing machine is operating. However, the central processor (120) may control the operation of the ultraviolet detectors (104, 106) so that the receivers of the ultraviolet detectors (104, 106) and/or the associated photodetectors are only activated at times when a bank note is placed at a desired position in front of the ultraviolet detectors (104, 106). Accordingly, the bank note processing machine may operate in an energy efficient manner.

Figure 3:
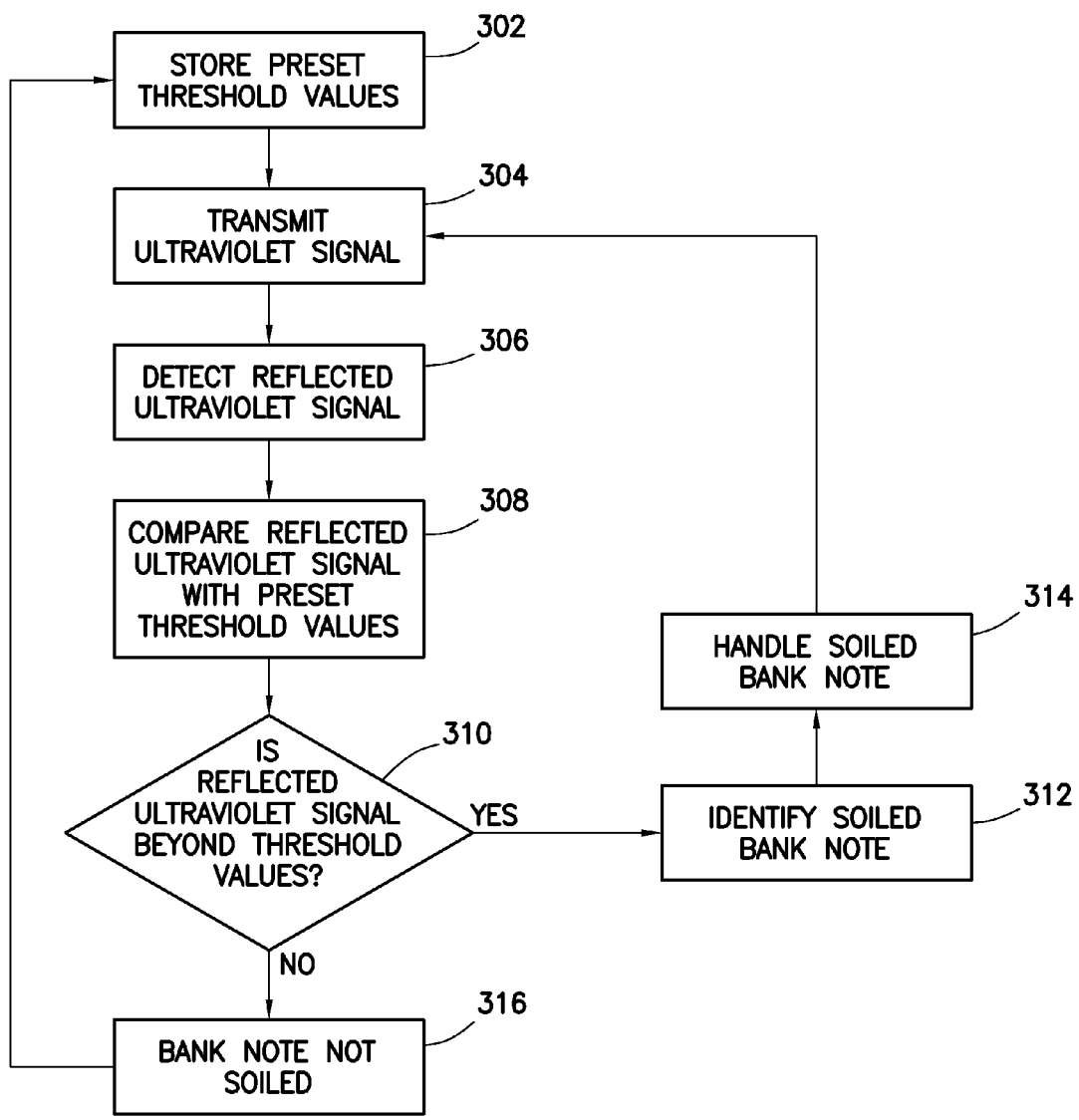
FIG. 3 is a flowchart representing the processing steps in accordance with an embodiment of the present disclosure.

FIG. 3 provides a flowchart of the processing steps taken by the central processor (120) when sensing a bank note (210) in accordance with an embodiment of the present disclosure. In one embodiment, each of the ultraviolet detectors (104, 106) perform the steps as shown in FIG. 3 and each can independently identify a bank note (210) as soiled. In another embodiment, only one ultraviolet detector may be used and the bank note (210) may be identified as soiled based on the conditions on only one of its two surfaces.

As shown in FIG. 3, at step 302 threshold values for the reflected ultraviolet signal are stored in a computer-readable media. In certain embodiments, the threshold values may include the soiling levels determined at the calibration step as discussed in more detail above. These threshold values are also referred to herein as the calibration data as discussed above. This computer readable-medium may be an integral part of the ultraviolet detectors (104, 106), may be part of the central processor (120) or may be communicatively coupled to the ultraviolet detectors (104, 106) or the central processor (120) through a wired or wireless network. The implementation of such wired or wireless networks is well known to those of ordinary skill in the art and will therefore, not be discussed in detail herein.

As discussed above, the calibration data stored in the computer-readable medium relate to the characteristics of a reflected ultraviolet signal from a surface of a soiled bank note. In one embodiment, the calibration data may be experimentally determined as discussed above. Specifically, bank notes may be visually inspected and a sample soiled bank note may be selected. The sample soiled bank note may be a bank note that it is soiled to the maximum acceptable limit. Alternatively, a number of sample soiled bank notes may be selected which are soiled at different level. The reflected ultraviolet signal from the selected soiled bank note may be analyzed and its characteristics (e.g. intensity, amplitude, etc) may be identified. These characteristics of the ultraviolet signal reflected from the soiled bank note may then be designated as the threshold values that may be used to identify soiled bank notes having different soiling levels as discussed above. In accordance with the present disclosure, a bank note is deemed to be soiled "beyond the threshold value" if it has a soiling level that is unacceptable to the user.

Next, at step 304, the transceiver (204 and/or 206) of the ultraviolet detector (104 and/or 106) may transmit an ultraviolet signal (as shown by arrows in FIG. 2) that is incident upon the surface of the bank note (210). This ultraviolet signal is then reflected from the bank note (210). At step 306, the reflected ultraviolet signal is detected by the transceiver (204 and/or 206) of the ultraviolet detector (104 and/or 106). As discussed above, in certain embodiments the ultraviolet detector (104 and/or 106) may include or be coupled to a photodetector to monitor the intensity of the reflected light. The ultraviolet detector (104 and/or 106) may relay the information regarding the characteristics of the reflected ultraviolet signal to the central processor (120) which then compares the characteristics of the reflected ultraviolet signal with the calibration data at step 308. Specifically, in certain embodiments, different soiling levels may be experimentally assigned to reflected lights having particular characteristics as discussed above. The characteristics of the reflected light from each bank note may then be compared with this calibration data to assign a soiling level to the bank note. In certain embodiments, the central processor (120) may perform this analysis and assign a soiling level to the bank note. Alternatively, the ultraviolet detector (104 and/or 106) may itself be equipped with an information handling system to compare the characteristics of the reflected ultraviolet signal with the calibration data. For instance, in certain embodiments, the amplitude of the reflected ultraviolet signal may be compared to predetermined amplitudes of reflected ultraviolet signals from a soiled bank note as identified at step 302. At step 310, it is determined if the reflected ultraviolet signal detected at step 306 has characteristics that fall beyond the threshold value. Specifically, at step 310, it is determined whether the soiling level of the particular bank note is unacceptable.

If yes, the process continues to step (312) and the central processor (120) identifies the bank note (210) as a soiled bank note. Next, at step 314 the soiled bank note will be handled. As would be appreciated by those of ordinary skill in the art, with the benefit of this disclosure, the soiled bank note may be handled in a number of ways. For instance, as discussed above in conjunction with FIG. 1, in one embodiment, the soiled bank note may be directed to the reject pocket 110. It may then be shredded or otherwise disposed of and replaced with a non-soiled bank note. Once the soiled bank note has been handled at step 314, the process returns to step 304 where the next bank note is directed to the ultraviolet detector (104, 106) and the process is repeated.

If at step 310 it is determined that the bank note (210) being analyzed is not a soiled bank note, the bank note (210) is passed along through the ultraviolet detector (104, and/or 106) and the process returns to step 304 and is repeated for subsequent bank notes.

In certain embodiments, the bank notes having soiling levels that fall within a preset range may be grouped together by the bank note processing machine. Specifically, once the soiling level of the bank note is determined at step 308, the bank note processing machine may direct the bank note to a particular pocket that is assigned to bank notes having that soiling level. In this manner, bank notes having different soiling levels may be grouped together and handled as desired by the user.

While the present embodiment depicts use of a pair of ultraviolet detectors (104, 106), other embodiments may use one or multiple detectors. Specifically, when using a pair of detectors as shown in FIGS. 1 and 2, each detector may analyze one of the two surfaces of the bank note (210). However, in certain embodiments one detector may be used to analyze a single surface of the bank note (210) with the result of that analysis being indicative of the soiling of the bank note (210) as a whole. Alternatively, multiple ultraviolet detectors may be used to provide system redundancy.

In accordance with an embodiment of the present disclosure, the ultraviolet detectors (104, 106) may be communicatively coupled to an information handling system through a wired or wireless network. The information handling system may include, or be communicatively coupled to a computer-readable medium which includes instructions allowing the information handling system to perform the methods disclosed herein.

Therefore, the present disclosure is well-adapted to carry out the objects and attain the ends and advantages mentioned as well as those which are inherent therein. While the disclosure has been depicted and described by reference to exemplary embodiments of the disclosure, such a reference does not imply a limitation on the disclosure, and no such limitation is to be inferred. The disclosure is capable of considerable modification, alteration, and equivalents in form and function, as will occur to those ordinarily skilled in the pertinent arts and having the benefit of this disclosure. The depicted and described embodiments of the disclosure are exemplary only, and are not exhaustive of the scope of the disclosure. Consequently, the disclosure is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A method for handling soiled bank notes comprising:
    directing a bank note to an ultraviolet detector;
    transmitting an ultraviolet signal from the ultraviolet detector to a white portion of the bank note;
    receiving a reflected ultraviolet signal from the white portion of the bank note at the ultraviolet detector;
    analyzing the reflected ultraviolet signal;
    identifying biological soiling for the bank note based on analysis of the reflected ultraviolet signal indicating a wavelength of approximately 470 nanometers; and
    handling the bank note based on the identified biological soiling.

2. The method of claim 1, wherein handling the soiled bank note comprises at least one of grouping the bank note with one or more other bank notes having biological soiling and shredding the soiled bank note.

3. The method of claim 1, wherein the transmitted ultraviolet signal has a wavelength between approximately 280 nm and approximately 380 nm.

4. The method of claim 1, further comprising analyzing intensity of the reflected ultraviolet signal with a photodetector, wherein identification of biological soiling for the bank note is further based on the analysis of intensity of the reflected ultraviolet light.

5. A system for identification of soiled bank notes comprising:
    an ultraviolet detector comprising a transmitter and a receiver;
    a belt, wherein the belt carries a bank note to the ultraviolet detector;
        wherein the transmitter transmits an ultraviolet signal to a white portion of the bank note;
        wherein the ultraviolet signal is reflected from the white portion of a surface of the bank note;
        wherein the receiver receives the reflected ultraviolet signal; and
    an information handling system communicatively coupled to the ultraviolet detector;
        wherein the information handling system determines biological soiling of the bank note based on the reflected ultraviolet signal having a wavelength of approximately 470 nanometers.

6. The system of claim 5, further comprising a pocket, wherein the bank note is directed to the pocket if biological soiling is determined.

7. The system of claim 5, wherein the information handling system comprises a computer-readable medium.

8. A method for identifying a soiled bank note comprising:
    storing calibration data in a computer readable medium, wherein the calibration data includes a reflected wavelength of 470 nanometers that identifies biological soiling for a bank note having a reflected ultraviolet signal from a white portion of the bank note of approximately 470 nanometers;
    directing a bank note to a first ultraviolet detector, wherein the first ultraviolet detector corresponds to a first surface of the bank note;
    transmitting a first ultraviolet signal from the first ultraviolet detector to a white portion of the first surface of the bank note and receiving a first reflected ultraviolet signal from the white portion of the first surface of the bank note at the first ultraviolet detector;
    comparing a characteristic of the first reflected ultraviolet signal with the calibration data;
    determining biological soiling for the bank note based on the comparison of the characteristic of the first reflected ultraviolet signal with the calibration data.

9. The method of claim 8, further comprising:
    providing a second ultraviolet detector, wherein the second ultraviolet detector corresponds to a second surface of the bank note;
    directing the bank note to the second ultraviolet detector;
    transmitting a second ultraviolet signal from the second ultraviolet detector to a second surface of the bank note and receiving a second reflected ultraviolet signal from the second surface of the bank note at the second ultraviolet detector;
    comparing a characteristic of the second reflected ultraviolet signal with the calibration data; and
    determining if the bank note is a soiled bank note based on the comparison of the characteristic of the second reflected ultraviolet signal with the calibration data.

10. The method of claim 9, wherein the calibration data is experimentally determined.

11. The method of claim 9, wherein the bank note is directed to a pocket if the bank note has a soiling level exceeding a threshold soiling level.

12. The method of claim 9, wherein the bank note is shredded if the bank note has a soiling level exceeding a threshold soiling level.

13. The method of claim 9, wherein directing a bank note to a first ultraviolet detector comprises carrying the bank note to the first ultraviolet detector on a belt.

14. The method of claim 9, wherein the first ultraviolet signal has a wavelength between approximately 280 nm and approximately 380 nm.

15. The method of claim 9, wherein comparing a characteristic of the first reflected ultraviolet signal with the calibration data comprises comparing an intensity of the first reflected ultraviolet signal with the calibration data.

* * * * *